US012559370B2

(12) United States Patent
Birch et al.

(10) Patent No.: US 12,559,370 B2
(45) Date of Patent: Feb. 24, 2026

(54) METHOD AND SYSTEM FOR OZONE GENERATION

(71) Applicant: 13482073 CANADA INC., Markham (CA)

(72) Inventors: Peter Birch, Markham (CA); Ching Kuo Pai, Markham (CA)

( * ) Notice: Subject to any disclaimer, the term of this patent is extended or adjusted under 35 U.S.C. 154(b) by 954 days.

(21) Appl. No.: 17/699,488

(22) Filed: Mar. 21, 2022

(65) Prior Publication Data
US 2023/0294989 A1 Sep. 21, 2023

(51) Int. Cl.
| | |
|---|---|
| *C01B 13/10* | (2006.01) |
| *A61L 2/20* | (2006.01) |
| *A61L 2/202* | (2026.01) |
| *A61L 2/24* | (2006.01) |
| *A61L 9/015* | (2006.01) |
| *B01J 19/12* | (2006.01) |

(52) U.S. Cl.
CPC .............. *C01B 13/10* (2013.01); *A61L 2/202* (2013.01); *A61L 2/24* (2013.01); *A61L 9/015* (2013.01); *B01J 19/123* (2013.01); *A61L 2202/11* (2013.01); *A61L 2202/14* (2013.01); *A61L 2209/12* (2013.01)

(58) Field of Classification Search
None
See application file for complete search history.

(56) References Cited

U.S. PATENT DOCUMENTS

| | | | | |
|---|---|---|---|---|
| 2009/0263499 A1* | 10/2009 | Platt, Jr. | .................... | F24F 8/24 |
| | | | | 422/291 |
| 2014/0205504 A1* | 7/2014 | Khoshbin | ............... | C01B 13/10 |
| | | | | 422/186.3 |
| 2021/0283285 A1* | 9/2021 | Li | ............................. | A61L 2/10 |

FOREIGN PATENT DOCUMENTS

CN        105003981 A  * 10/2015

OTHER PUBLICATIONS

English translation of CN-105003981-A Description (Year: 2015).*
Collins Dictionary. "Definition of 'additional'". Accessed online at https://www.collinsdictionary.com/dictionary/english/additional on Apr. 3, 2025. (Year: 2025).*
NobleLight. Amelgam UV lamps for disinfection and oxidation, 2025. Accessed electronically at https://www.noblelight.com/en/etc/products_and_solutions/uv_lamps_and_systems/uv_lamps/uv_amalgan_lamps/uv_amalgam_lamps.html#tabs-43508-3 on Aug. 18, 2025. (Year: 2025).*

* cited by examiner

*Primary Examiner* — Anthony J Zimmer
*Assistant Examiner* — Zachary John Baum

(57) ABSTRACT
A method and system of generating ozone gas. The method comprises receiving a stream of ambient air that includes at least oxygen gas, generating ozone gas based upon applying ultraviolet (UV) irradiation provided in accordance with a wavelength of 185 nanometer (nm) to at least a portion of the oxygen gas, the UV irradiation provided via an optical lamp module powered by a direct current (DC) voltage battery source, producing a modified air stream in accordance with the generating, and exhausting the modified air stream, the modified air stream having a higher concentration of ozone gas as compared with a trace concentration of ozone gas that is constituted in the stream of ambient air.

7 Claims, 6 Drawing Sheets

300

400

402

405

402a

402b

402c

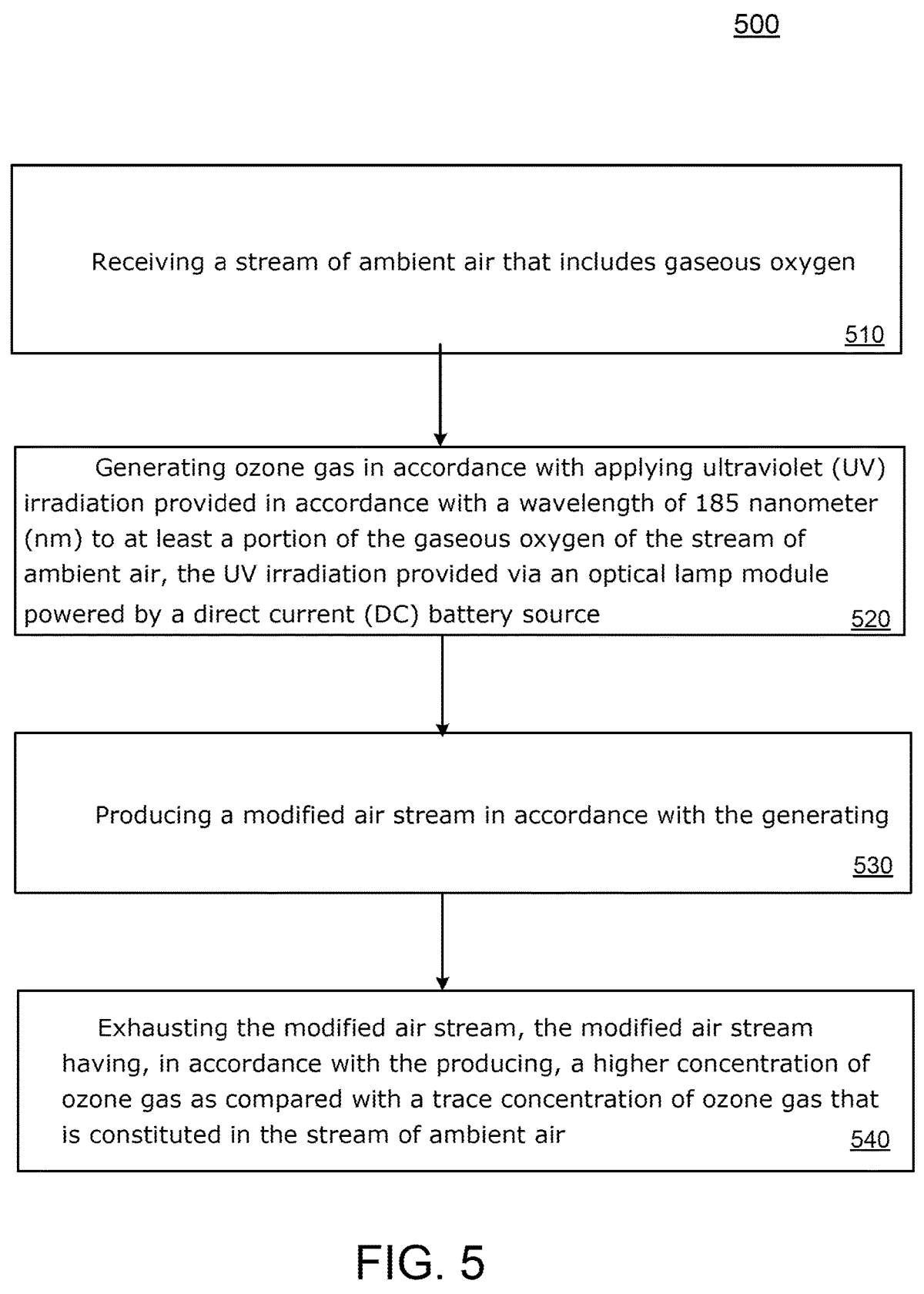

500

```
┌──────────────────────────────────────────────────────────┐
│                                                            │
│   Receiving a stream of ambient air that includes gaseous oxygen │
│                                                            │
│                                                     510    │
└──────────────────────────────────────────────────────────┘
                              │
                              ▼
┌──────────────────────────────────────────────────────────┐
│   Generating ozone gas in accordance with applying ultraviolet (UV) │
│ irradiation provided in accordance with a wavelength of 185 nanometer │
│ (nm) to at least a portion of the gaseous oxygen of the stream of │
│ ambient air, the UV irradiation provided via an optical lamp module │
│ powered by a direct current (DC) battery source        520 │
└──────────────────────────────────────────────────────────┘
                              │
                              ▼
┌──────────────────────────────────────────────────────────┐
│                                                            │
│   Producing a modified air stream in accordance with the generating │
│                                                            │
│                                                     530    │
└──────────────────────────────────────────────────────────┘
                              │
                              ▼
┌──────────────────────────────────────────────────────────┐
│   Exhausting the modified air stream, the modified air stream │
│ having, in accordance with the producing, a higher concentration of │
│ ozone gas as compared with a trace concentration of ozone gas that │
│ is constituted in the stream of ambient air        540    │
└──────────────────────────────────────────────────────────┘
```

FIG. 5

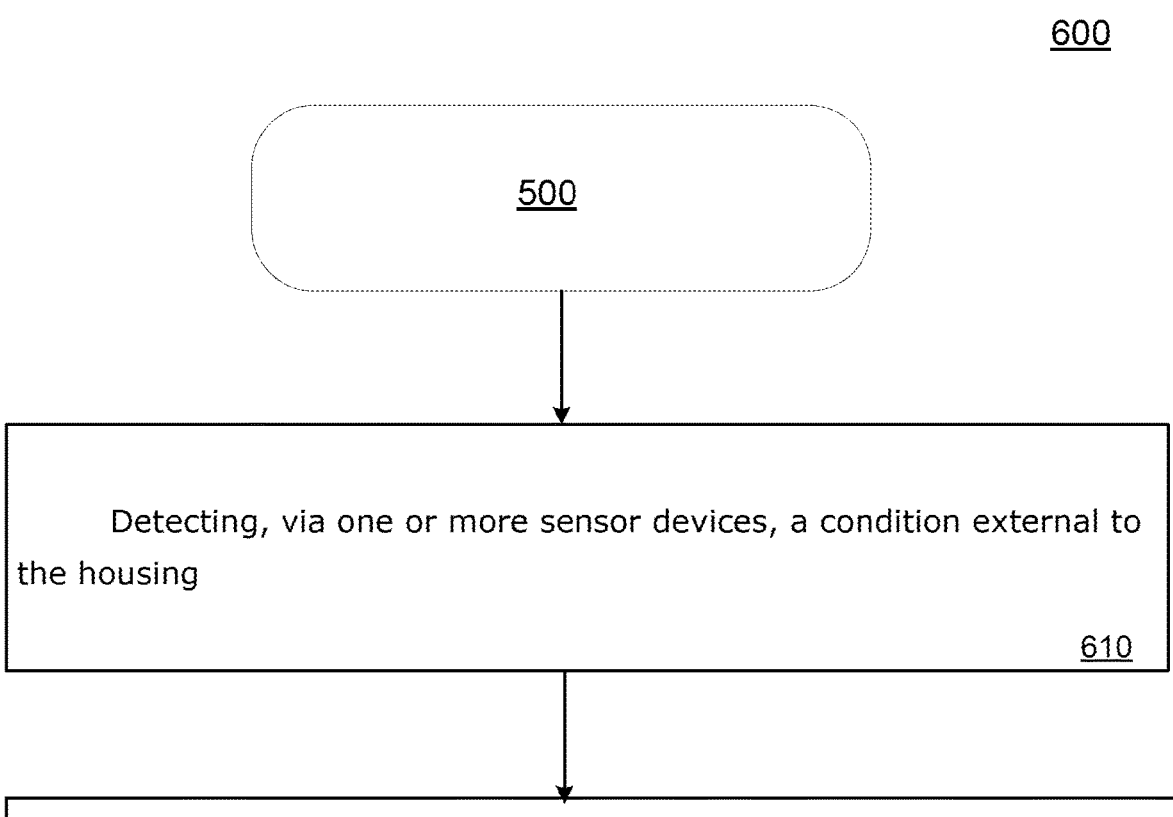

600

500

Detecting, via one or more sensor devices, a condition external to the housing

610

Switching, responsive to the detecting, to a second mode of operation that produces a second modified airstream, the second modified airstream comprising at least one of: (i) a higher concentration of ozone gas than the first modified airstream, and (ii) a higher flowrate of the exhausting as compared with the first modified airstream

METHOD AND SYSTEM FOR OZONE GENERATION

TECHNICAL FIELD

The disclosure herein relates to ozone generators and methods of operating such ozone generators.

BACKGROUND

Ozone, a trace gas in the earth's atmosphere, is formed by molecules made up of 3 oxygen atoms (O3) and has the characteristic of being a powerful oxidizing agent proven to be highly effective in killing bacteria, fungi and molds and inactivating viruses. Ozone can be used for the treatment of potentially contaminated surfaces, water, and ambient air thanks to its powerful germicidal effect on a wide spectrum of microorganisms. Ozone created by various kinds of ozone generators can reach every corner of the environment of a single room or a larger space, without leaving any undesired residues. The effectiveness of ozone in treating microorganisms, especially bacteria and viruses is related to various factors, such as ozone concentration, the temperature of the environment, humidity of the environment and exposure time.

BRIEF DESCRIPTION OF THE DRAWINGS

FIG. 5 illustrates, in an example embodiment, a method of operation of an ozone generating device.

FIG. 6 illustrates, in yet another example embodiment, a method of operation of an ozone generating device in accordance with a higher order method of operation.

DETAILED DESCRIPTION

Figure 1:
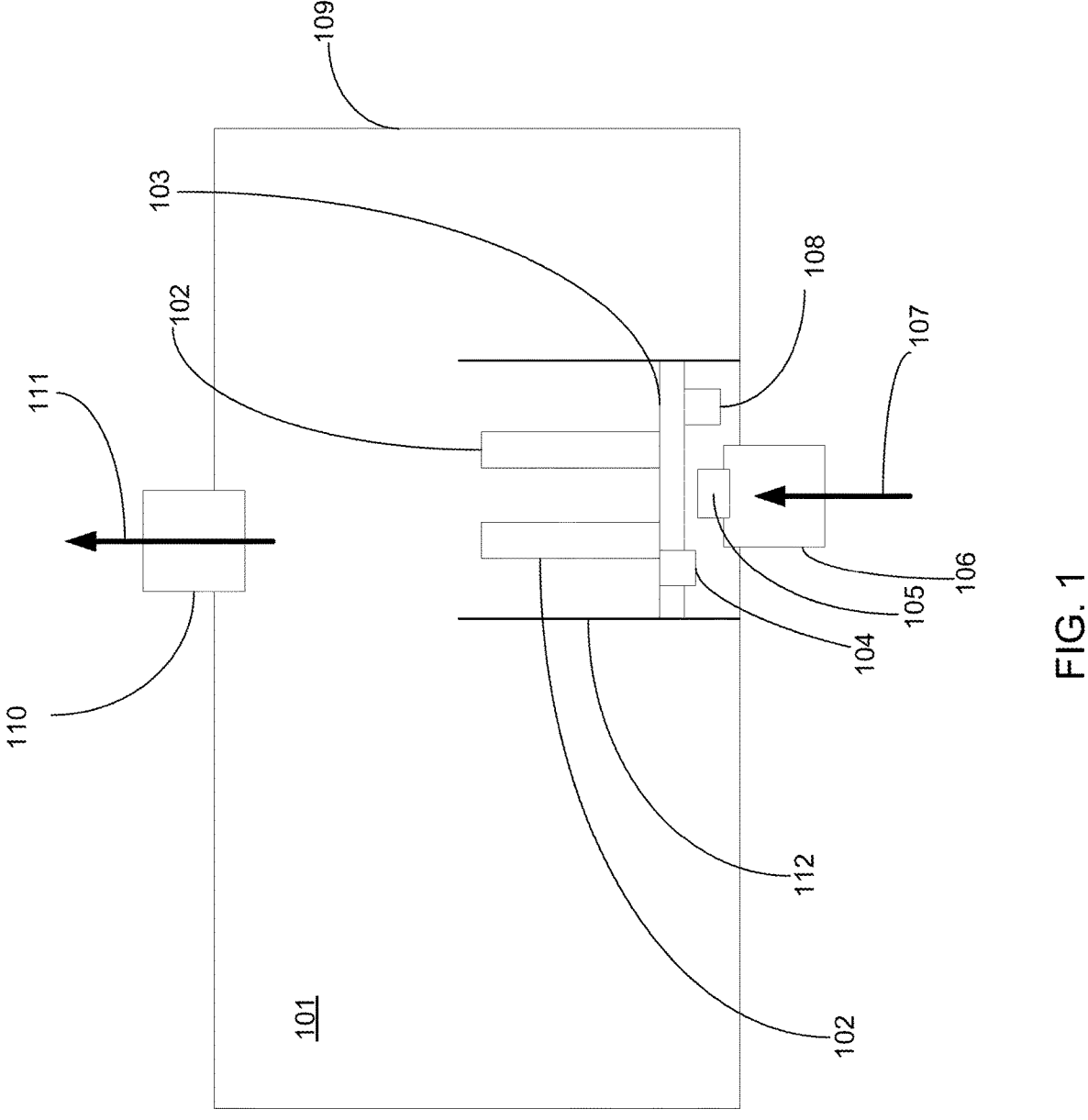
FIG. 1 illustrates, in an example embodiment, an ozone generating device.

Embodiments herein recognize the need for advantageously leveraging the anti-viral and anti-microbial attributes of ozone gas within an at least partially closed environment of living space, while controlling ozone gas concentration within acceptable levels in order to avoid adverse effects on human beings and other living creatures. Embodiments herein also recognize the need for ozone gas generators to operationally ramp up and swiftly attain desired ozone gas concentrations in the given living space, yet without compromising safety of any beings occupying that living space. In particular, embodiments herein provide for an ozone gas generating device capable of operating in both a regular mode of operation as well as a higher order mode of operation as characterized by increased rate of generation of ozone gas, somewhat analogous to a "turbocharged" mode of operation, but only upon ascertaining or sensing that it would be safe to do so, thus avoiding unduly high and unsafe high concentration levels that could adversely affect living beings currently occupying an at least partially enclosed room or similar living space.

Provided is a method of generating ozone gas. The method comprises receiving a stream of ambient air that includes gaseous oxygen, generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source, producing a modified air stream in accordance with the generating and exhausting the modified air stream, the modified air stream having, in accordance with the producing, a higher concentration of ozone gas as compared with a trace concentration of ozone gas that is constituted in the stream of ambient air. In one embodiment having a heightened safety protocol, a remote motion sensor device can be used to detect that no human persons or living creatures are active within the surroundings, such as an enclosed room in which the ozone gas generating device is located, before switching to the second mode of operation having increased rate of generation or production of ozone gas. A second modified airstream generated in this higher order, or "turbocharged", mode of operation can comprise a higher concentration of ozone gas than the first modified airstream, and optionally also generated with a higher flowrate of exhausting as compared with the first modified airstream. In this manner, a higher rate of production of ozone gas can be generated within a given time period for dissemination into the surroundings safely while avoiding potentially adverse effects on living occupants in the space.

Also provided is an ozone gas generating system comprising a processor and a non-transitory memory including instructions. The instructions when executed by the processor causes the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air. The UV irradiation is provided via an optical lamp module powered by a direct current (DC) battery source. Generating the ozone gas produces a modified air stream constituted of ozone-rich air which has a higher concentration of ozone gas as compared with a trace concentration of ozone gas that is constituted in the stream of ambient air and is exhausted via exhaust port 110 to the surroundings.

Embodiments described herein can be implemented using programmatic modules, through the use of instructions that are executable by one or more processors. A programmatic module can include a program, a sub-routine, a portion of a program, or a software component or a hardware component capable of performing one or more stated tasks or functions. As used herein, a programmatic module can exist on a hardware component independently of other modules or components, or can be a shared element of other modules, programs or machines.

One or more embodiments described herein provide that methods, techniques, and actions performed in an ozone generating device and system are performed programmatically, or as a computer-implemented method. Programmatically, as used herein, means through the use of code or computer-executable instructions. These instructions can be stored in one or more memory resources accessible to the ozone gas generating device.

Device and System

FIG. 1 illustrates, in a diagrammatic embodiment not necessarily depicted to scale, ozone generating device 101. In one embodiment, ozone generating device 101 includes housing 109 having ingress port 106 for ambient air stream 107 and exhaust port 110 for egress of ozone-rich air stream 111. Controller module 103 may be manifested in a printed circuit board facilitating electronic interconnection with one or more optically irradiating lamps 102 providing ultraviolet irradiation in a wavelength of 185 nanometers (nm), with direct current (DC) battery 104 providing an electrical power source and being at least partly enclosed within protective cylindrical enclosure 112. Local ozone gas concentration sensor 108 may be electrically interconnected to controller module 103. One or more airflow pressure differential pressure-inducing fans or similar device 105 may be deployed proximate ingress port 106 and be capable of operation in variable airflow pressure rates that induce higher or lower airflow of ambient air into ozone generating device 101 via ingress port 106, and at least partly influencing exhaust air stream 111 at correspondingly higher and lower flow rates.

Figure 2:
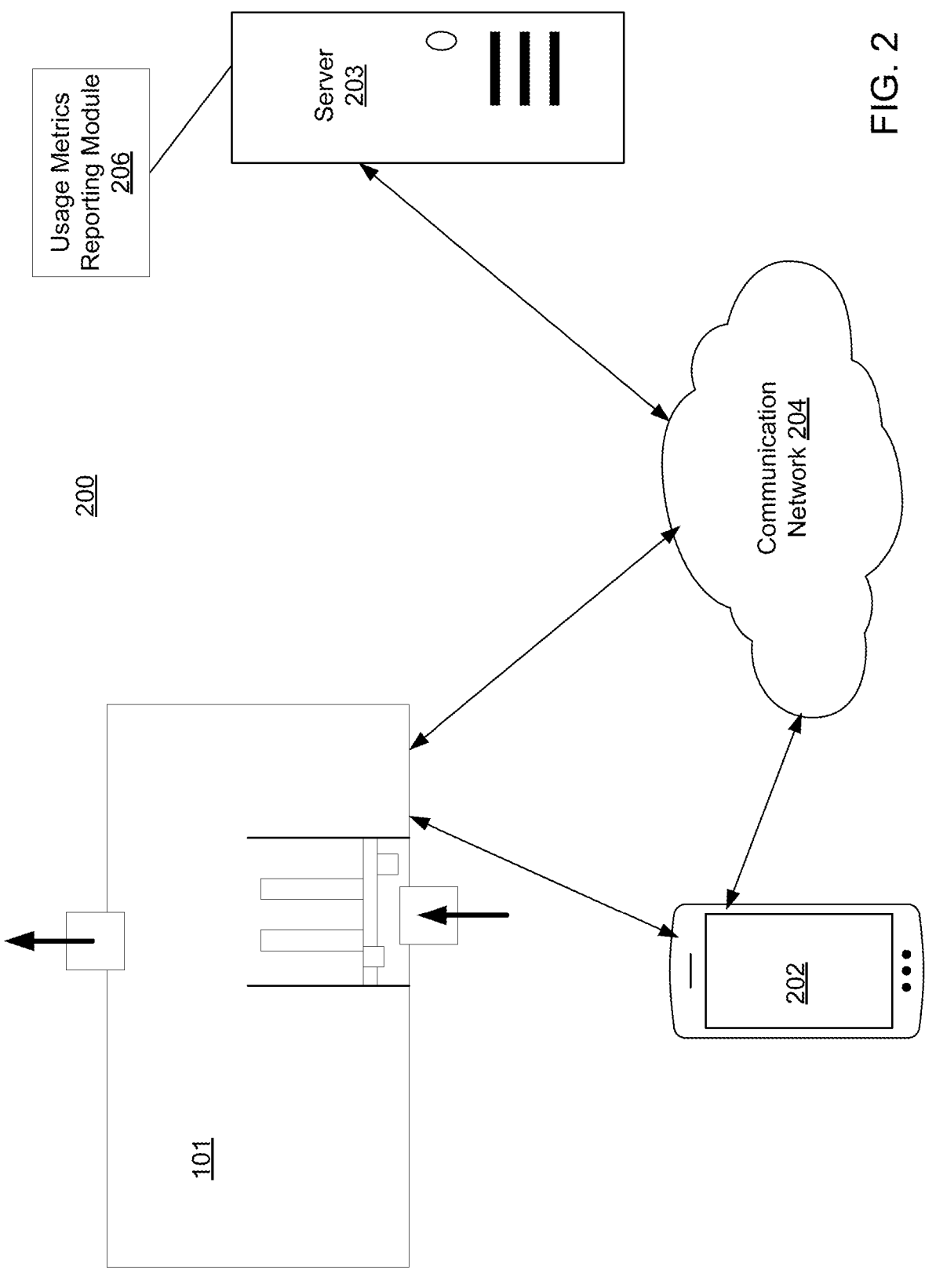
FIG. 2 illustrates, in an example embodiment, an ozone generating system including an ozone generating device.

FIG. 2 illustrates, in an example embodiment, ozone generating system 200 including ozone generating device 101. Ozone generating device 101 is communicatively coupled with mobile device 202 which may be such as a mobile phone or tablet computing device. Ozone generating device 101 may also be communicatively coupled, in a cloud-based system as depicted, with server computing device 203 via communication network 204 which can in some embodiments be an internet or similar wide area or telecommunication-based connection. In embodiments, mobile device 202 can be communicatively linked to ozone generating device 101 via wireless communication protocols including, but not limited to, Bluetooth, Wi-Fi, LoRa or RFID. In some embodiments, mobile phone device 102 may include a software application that enables communication, either directly via wireless communication or via cloud based system 200 via communication network 204, with ozone gas generating device 101 in order to set or apply desired threshold values or acceptable ranges of ozone gas concentration, for instance as sensed by local ozone gas concentration sensor device 108.

In some embodiments, usage metrics and reporting module 206 of server 203 within system 200 can acquire data, during or subsequent to a usage session, from controller module 103 of ozone generating device 101. For instance, data transmissions from controller module 103 of ozone generating device 101, can include such as, but not limited to, one or more of user or device account information, geo-location information, timestamp information, recent and accumulated historical ozone gas generation metrics during deployment, for example. In embodiments, server 203 can be maintained at a remotely located provider service or monitoring authority that is communicatively accessible via communications network 204. It is contemplated that, in some variations, at least part of the usage metrics and reporting functionality attributed to usage metrics and reporting module 206 of server 203 as described herein can be deployed by way of a software application stored in a memory of mobile computing device 202 for execution thereon. In some embodiments, mobile computing device 202 can communicatively access server 203 via communication network 204.

Figure 3:
FIG. 3 illustrates, in an example embodiment, a configuration of an ultraviolet lamp deployed in an ozone generating device.

FIG. 3 illustrates, in an embodiment, example architecture 300 of controller module 103 of ozone generating device 101 as deployed within ozone generating system 200. Controller module 103, in embodiments, may include processor 301, memory 302 and be interconnected with UV irradiation lamp(s) 102, power source DC battery 304 which may be for instance a low power DC battery or similar power source operating in a range between 1.2V and 20V, and communication interface 307 that is communicatively coupled with communication network 204. Processor 301 can be implemented in an application specific integrated circuit (ASIC) device or field programmable gate array (FPGA) device, in some embodiments. Memory 302 may be such as, but not limited to, a random-access memory. Controller module 103 can also be coupled with ozone gas concentration sensor devices, including local ozone gas concentration sensor device 305 this is positioned within housing 109 and remote ozone gas concentration sensor device 305 that is positioned remotely, and external, from housing 109, such as in a room within which ozone generating device 101 is located and deployed. In embodiments, controller module 103 can also be coupled with remote motion sensor device (s) 309 to detect human presence, as inferred from motion, or lack thereof, with the area surrounding ozone generating device 101. Remote ozone gas concentration sensor device 305 and remote motion sensor device (s) 309 may be communicatively coupled with controller module 103 via wireless communication employing Wi-Fi or similar wireless communication protocols as described herein.

Controller module 103 may also include capability for communicatively accessing wireless communication signals, including but not limited to any of Bluetooth, Wi-Fi, LoRa, RFID, and global positioning system (GPS) signals, and incorporate communication interface 307 for communicatively coupling to communication network 104, such as by sending and receiving data transmissions. Controller module 103, in some embodiments, can also incorporate GPS position location functionality based on GPS receiver and transmitter circuitry for accessing and enabling transmission of operational metrics associated with deployment of ozone generating device 101 such as, but not limited to, account information associated with ozone generating device 101, location information, timestamp information and ozone gas operational data associated with ozone generating device 101. Controller module 103 can be communicatively coupled with variable air flow generating device (s) 309, which in embodiments may be airflow pressure differential pressure-inducing fans or devices 105 as described in regard to FIG. 1.

Ozone generator logic module 310 of controller module 103, in embodiments, can be constituted of computer processor-executable code stored in memory 302 that are executable in processor 301, to accomplish ozone gas generation functionality as described herein, associated with usage or deployment of ozone generating device 101. In one embodiment, the software instructions or programs, including any updates thereof, constituting ozone generator logic module 310 can be downloaded to memory 202 by accessing and downloading, via communication network 204, from a remote server computing device, including from server 203, or from mobile computing device 202 via wireless communication protocols as described herein.

Ozone generator logic module 310 of controller module 103, in embodiments, enables deployment of ozone gas generator 101 within ozone gas generating system 200 and includes, in non-transitory memory 302, logic instructions that are executable in processor 301. The instructions when executed by processor 301 cause the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air, the UV irradiation provided via an optical lamp module powered by a direct current (DC) battery source, producing a modified air stream in accordance with the generating and exhausting the modified air stream, the modified air stream having a higher concentration of ozone gas as compared with a trace concentration of ozone gas that is constituted in the incoming stream of ambient air via ingress port 106.

Ozone generator logic module 310 of controller module 103, in some embodiments, also includes, in non-transitory memory 302, logic instructions that are executable in processor 301 to adjust the rate of generating ozone gas based on local and remote sensors 305, 306, and also based on remote motion sensor 308. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 50 parts per billion (ppb) and 100 ppb, though it is contemplated that other ranges or values can be implemented.

Figure 4:
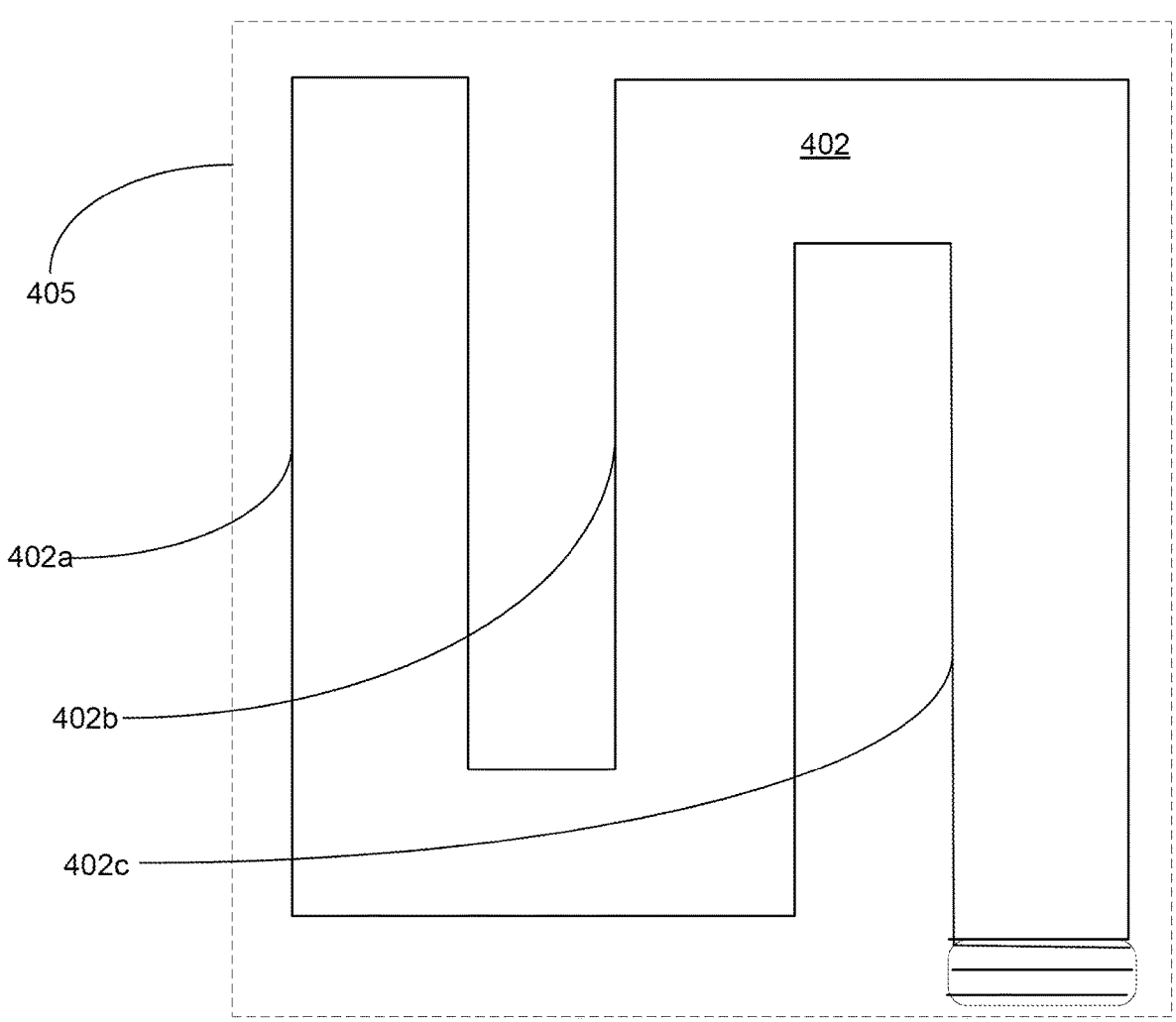
FIG. 4 illustrates, in an embodiment, an example architecture of an ozone generating device deployed in an ozone generating system.

FIG. 4 illustrates an example embodiment configuration 400 of ultraviolet lamp 402 for deployment in ozone generating device 101. In an embodiment of optical lamp module 102, optical lamp 402, in a diagrammatic representation not drawn to scale, includes at least one irradiating surface configured at least partly in parallel sections 402a, 402b, 402c within a square area 405 bounding an overall length of the irradiating surface. In this manner, a most compact irradiation source providing maximum optical irradiation surface area for ozone gas generation can be deployed, that minimizes a size of the irradiation lamp module 102 thereby allowing ozone generating device 101 to be deployed in a most compact and portable physical configuration.

Methodology

FIG. 5 illustrates, in an example embodiment, method of operation 500 of ozone generating device 101. Examples of method steps described herein are related to deployment and use of ozone generating device 101 as described herein. According to one embodiment, the techniques are performed in processor 301 executing one or more sequences of software logic instructions that constitute ozone generator logic module 310 of controller module 103. In embodiments, instructions constituting ozone generator logic module 310 may be read into memory 302 from machine-readable medium, such as memory storage devices. Executing the instructions of ozone generator logic module 310 stored in memory 302 causes processor 301 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 510, receiving a stream of ambient air that includes gaseous oxygen via an ingress port within a housing of an ozone generating device.

At step 520, generating ozone gas in accordance with applying ultraviolet (UV) irradiation provided in a wavelength of 185 nanometer (nm) to at least a portion of the gaseous oxygen of the stream of ambient air, the UV irradiation provided via an optical lamp module powered by a direct current (DC) battery source. The shorter 185 nanometers wavelength of UV irradiation generates ozone by reacting with oxygen in the ambient air stream to break it into atomic oxygen, making available a highly unstable oxygen atom that then combines with oxygen in the ambient air stream to form ozone.

At step 530, producing a modified air stream in accordance with the generating. In some embodiments, either one of local ozone gas sensor device 305 or remote ozone gas sensor device 306 can sense ozone concentration being produced by ozone generator device 101, and if the sensed ozone gas concentration level is higher than a predetermined threshold level, processor 301 can operate optical lamp module 102 using an intermittent, duty cycle-based, on/off powered pattern that moderates ozone gas generation into a more acceptable range, and then to maintain it within that range. In some example embodiments, between 50-500 ppb may be predetermined as such an acceptable range, though other ppb values may be deployed. In embodiments, the threshold levels deemed acceptable can be set, or changed from a pre-existing value or values via mobile phone device 202.

At step 540, exhausting the modified air stream via an exhaust port of the housing, the modified air stream having a higher concentration of ozone gas as compared with a trace concentration of ozone gas that is constituted in the stream of ambient air.

In yet another variation, the method can include transmitting, to a computing device such as a remote server computing device, one or more of account information, location information and timestamp information associated with ozone generator device 101 and details of its operation within ozone gas generating system 200.

FIG. 6 illustrates, in yet another example embodiment, a further method of operation 600 of ozone generating device 101. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space as determined in accordance with remote motion sensor device 308, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 5 parts per billion (ppb) and 1,000 ppb. However, it is contemplated that other ranges or values can be deployed; for instance, in a range from 50 ppb to 500 ppb of ozone gas concentration.

At step 610, detecting, via one or more remote sensor devices 306, a condition that is external to the housing. In one embodiment, the condition external to the housing can be determined as being an absence of a person within a predetermined area around the housing, using one or more remote motion sensor device(s) 308.

In a further variation, using one or more remote ozone gas concentration sensor device(s) 306, the condition external to the housing can be determined as a concentration of ozone gas being below a predetermined threshold concentration, for instance in a range of 50 to 500 ppb, within a predetermined area around the housing of ozone gas generating device 101.

At step 620, switching, responsive to the detecting, to a second mode of operation that produces a second modified airstream, the second modified airstream comprising at least one of: (i) a higher concentration of ozone gas than the first modified airstream, and (ii) a higher flowrate of the exhausting as compared with the first modified airstream. In this manner, a higher rate of production of ozone gas can be generated within a given time period and subsequently disseminated into the surroundings. In one embodiment having a heightened safety protocol, remote motion sensor device 308 can be used to detect that no human person(s) are active or occupying the surroundings, such as an enclosed room in which gas generating device 101 is located, before switching to the second mode of operation having increased rate of generation or production of ozone gas.

In an embodiment, the optical lamp module includes one or more optical lamps, and the second mode of operation comprises activating at least one additional optical lamp of the optical lamp module.

In another variation, the higher flowrate of the second modified air stream is accomplished in accordance with varying an operational state of one or more pressure differential-inducing devices disposed at least partially within the housing. Such varying of operational state can be accomplished by activating additional fans, speeding up deployed fans, or any combination thereof, whereupon additional fans and/or fans operating at higher speeds accomplish higher ozone generation rates, and faster times to reach a given concentration of ozone gas, in accordance with the higher order, or "turbocharged", mode as described herein.

In yet another embodiment, the method includes terminating at least the second mode of operation, responsive to detecting that a concentration of ozone gas exceeds a predetermined threshold concentration in ppb in an area around the housing.

Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations of such does not preclude the inventor from claiming rights to such combinations.

What is claimed is:

1. A method of generating ozone gas, the method comprising:

receiving a stream of ambient air that includes gaseous oxygen;

generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source, wherein the optical lamp module is disposed within a housing of an ozone generating device having an ingress port and an exhaust port;

producing a first modified air stream during a first mode of operation in accordance with the generating;

detecting, via one or more sensor devices, a condition external to the housing;

switching, responsive to the detecting, to a second mode of operation that produces a second modified airstream, the second modified airstream having a higher flowrate than the first modified airstream;

receiving the stream of ambient air via the ingress port of the housing;

exhausting one of the first modified air stream and the second modified airstream via the exhaust port of the housing, the optical lamp module being disposed intermediate the ingress and exhaust ports; and detecting, using one or more proximity-based motion sensors, the condition external to the housing as being an absence of a person within a predetermined area around the housing;

wherein the second modified airstream comprises at least one of: (i) a higher concentration of ozone gas than the first modified airstream, and (ii) a higher flowrate of the exhausting as compared with the first modified airstream.

2. The method of claim 1 wherein the optical lamp module includes a first plurality of optical lamps activated during the first mode of operation in providing the first modified airstream, and the second mode of operation comprises activating at least one optical lamp of a second plurality of optical lamps of the optical lamp module.

3. The method of claim 1 wherein the higher flowrate is accomplished in accordance with varying an operational state of one or more pressure differential-inducing devices disposed at least partially within the housing.

4. The method of claim 1 further comprising detecting, using one or more ozone gas concentration sensors, the condition external to the housing as a concentration of ozone gas being below a predetermined threshold concentration within a predetermined area around the housing.

5. The method of claim 1 further comprising:

terminating, responsive to detecting that a concentration of ozone gas exceeds a predetermined threshold concentration in an area around the housing, at least the second mode of operation.

6. The method of claim 1 wherein the optical lamp module includes at least one irradiating surface configured at least partly in parallel sections within a square area bounding an overall length of the irradiating surface.

7. The method of claim 1 wherein the direct current (DC) battery source comprises an operating range of 1.2V to 20.0V.

* * * * *